United States Patent [19]

Somers, 3rd

[11] 4,381,011

[45] Apr. 26, 1983

[54] ENTERAL FEEDING APPARATUS AND METHOD

[76] Inventor: Lewis S. Somers, 3rd, 516 E. Gravers La., Wyndmoor, Pa. 19118

[21] Appl. No.: 260,332

[22] Filed: May 4, 1981

[51] Int. Cl.³ .............................................. A61B 5/00
[52] U.S. Cl. .................................... 128/635; 604/280
[58] Field of Search ................... 128/635, 213 R, 222, 128/223, 348, 780, 207.18

[56] References Cited

U.S. PATENT DOCUMENTS

| | | | |
|---|---|---|---|
| 2,168,867 | 8/1939 | George | 128/635 |
| 2,230,218 | 2/1941 | Asche | 128/276 |
| 3,043,309 | 7/1962 | McCarthy | 128/348 |
| 3,058,472 | 10/1962 | Thornton, Jr. | 128/348 |
| 3,373,735 | 3/1968 | Gallagher | 128/207.18 |
| 3,888,237 | 6/1975 | Mori | 128/635 |
| 4,078,562 | 3/1978 | Friedman | 128/213 |
| 4,134,405 | 1/1979 | Smit | 128/303 |

FOREIGN PATENT DOCUMENTS 2032780 5/1980 United Kingdom ................ 128/348

OTHER PUBLICATIONS

"Flexible pH Electrode for Esophageal and Gastro-Intestinal Research", Microelectrodes,Inc. Londonberry, N.H.

Primary Examiner—Lee S. Cohen
Attorney, Agent, or Firm—Woodcock, Washburn, Kurtz, Mackiewicz & Norris

[57] ABSTRACT

An improved system and method for enteric feeding of fluid material into a preselected portion of the gastrointestinal tract of a patient is disclosed. The system comprises an elongated flexible tube with a pH measuring device positioned thereon, a monitoring device capable of processing pH signals to determine the position of the tube, and fluid feed control.

15 Claims, 4 Drawing Figures

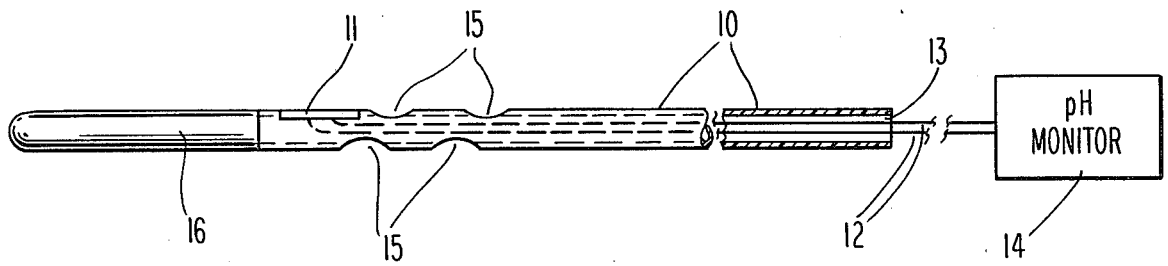
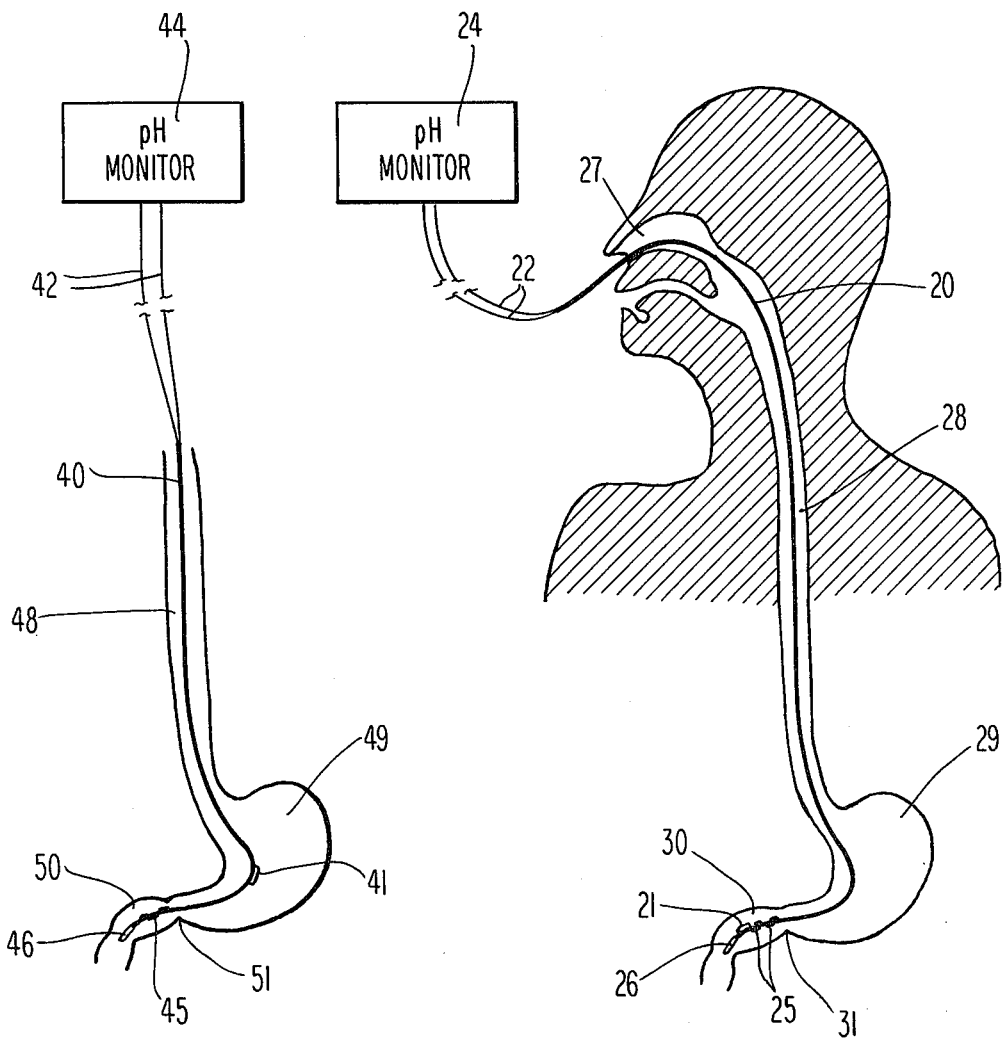

ENTERAL FEEDING APPARATUS AND METHOD

BACKGROUND OF THE INVENTION

This invention relates to an improved system and method for enteric feeding in which a fluid material may be introduced into a preselected portion of the gastro-intestinal tract of a patient, the system comprising an elongated flexible tube with a device for measuring pH positioned thereon, a monitoring device capable of processing a signal indicating the pH of the area adjacent to the pH measuring device to determine the position of the tube, and fluid feed control means.

Various types of tubes and intubating methods have been developed for use in diagnosing and treating problems related to the gastro-intestinal system. Physicians have used tubes introduced orally or nasally into the esophagus and stomach as means for furnishing food or medication to these areas. For example, U.S. Pat. No. 2,230,218 to Asche describes a gastro-intestinal treatment system utilizing a duplex treatment tube with separated passageways, one communicating with the stomach and the other with the duodenum. Other examples of systems and methods relating to gastro-intestinal intubation are described in U.S. Pat. No. 3,043,309 to McCarthy and U.S. Pat. No. 4,134,405 to Smit.

Intubation procedures may also be useful for diagnostic purposes. For example, U.S. Pat. No. 3,888,237 to Mori describes a pH-measuring device used in an endoscope which may be used to measure the pH of a liquid present in a living body, such as gastric juice oozing from the inner walls of the stomach. Use of a small glass pH electrode has also been described as effective in monitoring the frequency and duration of stomach acid reflux into the esophagus. ("Flexible pH Electrode for Esophageal and Gastro-Intestinal Research", by Microelectrodes, Inc.).

While intubation systems are used in a number of ways and with a variety of apparatus, enteric feeding procedures still involve a number of problems. Positioning of the tube in the duodenum of the patient is an important part of an enteric feeding procedure. By placing the feeding portion of the tube (e.g. an area of tube containing openings which communicate with the area outside of the tube) in the duodenum, a patient may be given nourishment or medication in the form of fluid material with a much decreased hazard of regurgitation as occurs when the material is introduced into the stomach. Unfortunately the positioning of the tube is usually done with the need for X-ray or fluoroscope monitoring or by feel as accomplished by an experienced practitioner. Even if these methods are initially successful in positioning the tube in the preselected area, they are not useful for long range monitoring of the position of the portion of the tube which is in open communication with the preselected area of the gastro-intestinal tract. More particularly, if the feeding portion of the tube should slip from the duodenum back into the stomach during the process of introducing fluid material into the tube, the patient may experience a much increased danger of regurgitation which could result in asphixiation and death.

Thus it is an object of this invention to provide a system and method useful for introducing fluid material into a preselected area of the gastro-intestinal tract of a patient.

It is a further object of this invention to provide a system and method for enteric feeding in which the position of a feeding portion of a tube used in the system may be continuously determined by measuring and monitoring the pH of a body fluid.

It is another object of this invention to provide a system and method for enteric feeding in which the position of the feeding portion of the tube may be monitored without the use of X-rays.

It is yet another object of this invention to provide a system and method for enteric feeding which may include the automatic termination of feeding when a processed pH signal indicates the feeding portion of the tube is out of position.

These and other objects of the invention will become apparent from the following description of the invention.

SUMMARY OF THE INVENTION

The present invention provides a system for introducing fluid material into a preselected area of the gastro-intestinal tract of a patient. The system comprises an elongated flexible tube having a substantially axial lumen through which fluid can flow, with perforations or openings through and along a preselected portion of the distal end of the tube which communicate from the lumen to the outside of the tube, a pH measuring means positioned proximate to the distal end for generating a signal representative of the pH of the body fluid adjacent to the pH measuring device, and a signal processing device connected to the pH measuring device for processing the signals generated by the pH measuring device and for determining the position of a feeding portion of the tube as a function of the monitored pH.

A variety of materials are useful in constructing the tube portion of the system of this invention. These materials include silicon rubber, polypropylene, and polyvinyl chloride (PVC). A variety of sizes may be used so that the length and diameter of the tube may be varied according to the size of the patient or according to the necessity of using the tube for other purposes. Perforations, e.g. slits or holes, are formed along a preselected area of the tube to comprise a feeding portion of the tube so that when the tube is in position the perforations are positioned in the area into which fluid material is to be introduced. The distal end of the tube may be weighted to aid in initial positioning of the tube as is known in the art.

Initial positioning of the tube and subsequent monitoring of the position of the tube is accomplished by receiving and processing pH signals from a pH measuring device positioned proximate to the distal end of the tube and connected to a pH monitoring device. For example, the tube may be selectively positioned in the duodenum of a patient by utilizing the distinctly different range in pH values for the stomach as compared to that for the duodenum. Since the pyloric valve separates the stomach from the duodenum, there is a rather sharp contrast between the pH values of the stomach and the duodenum, such as in a ratio of up to about 12:2. Monitoring the pH value may be accomplished by processing a pH signal and comparing the processed signal, either on an absolute basis or on a relative change basis (% increase or decrease), with a preselected acceptable reference value. Thus the position of a tube may be monitored on a continuous basis. Further, this monitoring does not expose a patient to X-rays of radioactivity.

Any electrode capable of detecting the pH of body fluids may be utilized in the system of this invention, such as a unipolar or bipolar electrode with necessary means for attachment to the monitoring device and the patient as required. A variety of pH signal processing and position determining devices may also be used. One such system may comprise a glass electrode connected by electrical leads to a pH meter with digital display.

Fluid materials may be introduced into the proximal end of the tube by conventional techniques including the use of gravity feed methods and apparatus or controlled pump methods and apparatus. Introduction of the fluid material may be terminated automatically by installing a control device between the position determining device and the fluid introduction system. The control device may be set to terminate the flow of fluid material upon receipt of a signal which indicates the tube is out of position.

BRIEF DESCRIPTION OF THE DRAWINGS

FIG. 1 shows a perspective view of one embodiment of the tube portion of the system of this invention with an electrode positioned at about the end of the distal end of the tube.

FIG. 2 is a diagrammatic view showing the tube portion of the system of this invention with the distal end positioned in the duodenum of a patient.

FIG. 4 shows a diagrammatic view of the stomach and duodenum of a patient in which an alternate embodiment of the tube portion of the system has been positioned.

DETAILED DESCRIPTION OF THE DRAWINGS

Figure 3:
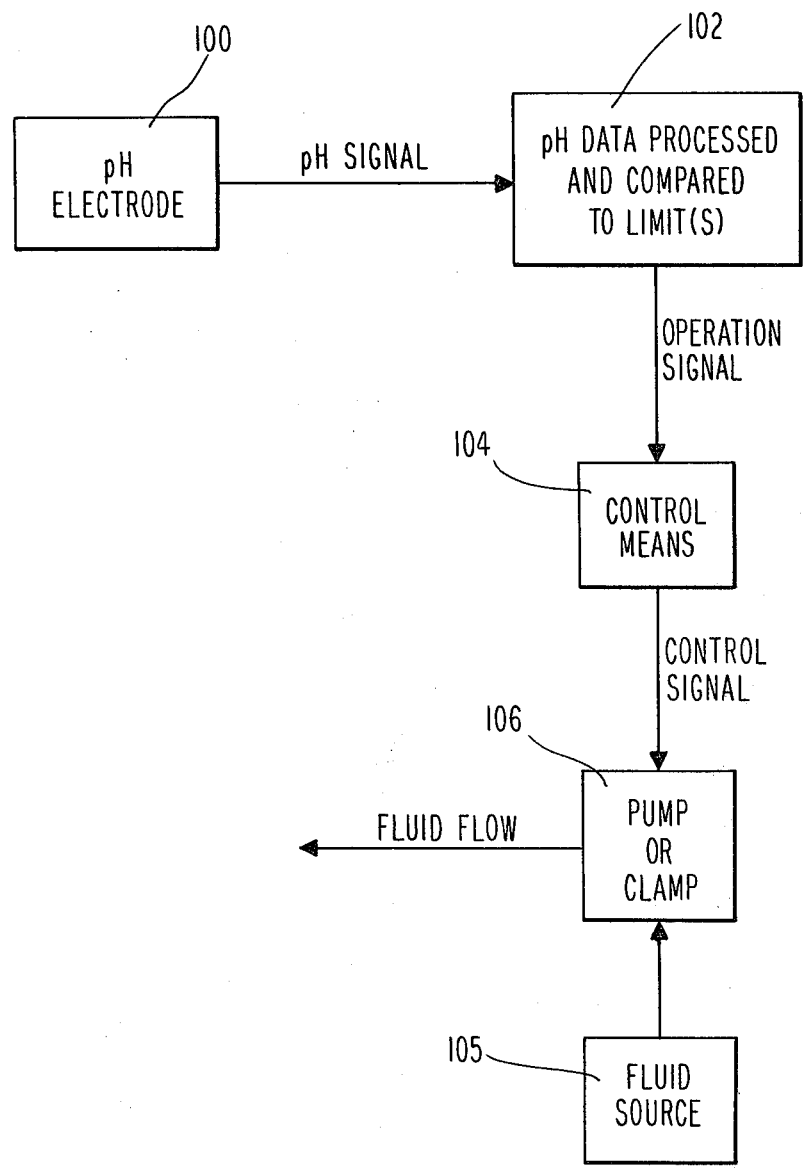
FIG. 3 is a block diagram showing one embodiment of the system of this invention.

FIG. 1 shows a perspective view of one embodiment of a tube structure of the system of this invention showing a tube portion 10 in which an electrode 11 has been positioned at about the distal end of the tube. The electrode 11 is selected to be capable of measuring the pH value of body fluid adjacent to the electrode 11 and is connected by means of electrical leads 12 extending through a substantially axial lumen 13 to a pH monitoring device 14. The tube 10 contains perforations or openings 15 therethrough which extend along a preselected portion of tube 10, and which communicate from the lumen 13 to an outside area of the tube. An optional weight 6 has been positioned at the extreme distal end of tube 10 and is conventionally used to facilitate the passage of a tube into the gastro-intestinal tract of a patient.

As shown in FIG. 1, electrode 11 is distal to the openings 15. However, another preferred embodiment is to position the electrode proximal to the openings, so that the electrode detects a shift of the tube tip toward the stomach before the perforations get there. Alternately, the electrode may be positioned within the perforations, i.e., between two of the openings 15.

FIG. 2 shows a diagrammatic view of the embodiment of the tube structure shown in FIG. 1 as positioned in a patient. The tube structure with tube portion 20 has electrode 21 positioned at about the distal end of the tube and at a distance selected to place a feeding portion of the tube with perforations 25 therethrough within the duodenum when in position. The electrode 21 is connected by electrical leads 22 to a pH monitoring device 24. As described in FIG. 1, the tube structure in FIG. 2 also has perforations 25 along a preselected area of the tube portion 20 and has a weight 26 at the extreme distal end. The tube structure is positioned by inserting the tube into the nasal passage 27 of the patient, with subsequent passage of the tube into the esophagus 28, stomach 29, and duodenum 30, of the patient. Initially the position of the distal end of the tube structure is located by monitoring the pH signals received from the electrode 21 and processed by pH monitoring device 24. There is a distinct change in pH value as the electrode passes from the stomach 29 into the duodenum 30 through pyloric valve 31. This change serves as an indication that the electrode and the portion of the tube structure in proximity to the electrode are positioned in the duodenum 30 of the patient. As previously described, perforations 25 are constucted along a preselected area of the tube portion 20. In this embodiment the preselected area is chosen to correspond to the area of the tube structure which will be in the duodenum 30 when the tube is in position. When in position these perforations 25 serve as ports for introducing final material selectively into the duodenum 30.

Once the tube structure has been positioned in the patient, its position may be continuously monitored by means of processing the signals received from electrode 21 on a continuing basis and comparing the processed signals to a reference value. A pH monitoring device 24 may be selected which either processes the pH signal as an absolute value for pH measured or as a percent of change (increase of decrease) in pH. The processed signal is then compared to a preselected limit or limits. An extreme change may indicate that the electrode 21 with its adjacent portion of the tube structure has slipped out of position in the duodenum 30 and back into the stomach 29. Corrective measures can then be taken such as stopping the flow of fluid material into the tube structure and/or repositioning the tube structure.

FIG. 3 shows a block diagram of one embodiment of the system of this invention in which a control means is used in conjunction with a controlled pump feeding apparatus. A pH electrode 100 generates a pH signal which is processed by pH monitoring device 102 to give either an absolute value for the pH of the body fluid measured or a percent change (increase or decrease) from the previously received pH signal. The monitoring device 102 then compares the pH data to a preselected acceptable limit, range, or percent change of pH value. If the measured pH value is outside of the preselected acceptable value, the pH monitoring device 102 generates an operation signal which instructs control means 104 to stop feeding. Control means 104 generates a control signal which stops the action of pump 106 from drawing fluid material from reservoir 105 thereby stopping the flow of fluid.

Alternatively, a gravity feed system may be used in place of the pump. With a gravity feed system, a clamp 106 may be engaged to cease feeding when a control signal is generated to close the clamp.

FIG. 4 shows a diagrammatic view of an alternate embodiment of the tubular structure suitable for use in the system of this invention as positioned in the stomach and duodenum of a patient. In this embodiment tubular structure with tube portion 40 has an electrode 41 positioned a predetermined distance from the distal end so that the electrode 41 will be placed in the stomach 49 of the patient when the distal end of the tube 40 with perforations 45 communicating the lumen to the outside of the tube are positioned in the duodenum 50 of a patient. Optional weight 46 is shown positioned at the extreme distal end of the tube structure to facilitate intubation of the patient. Electrode 41 is connected by leads 42 to a pH monitoring device 44. After initial positioning of the tube structure in the duodenum 50 of the patient, the position of the feeding portion of the tube structure is ascertained by the procedure previously described in FIG. 3. If the feeding portion of the tube with perforations 45 slips out of the duodenum 50 and back into the stomach 49, it will cause the portion of the tube structure with electrode 41 to be pushed up into the esophagus 48. Since the esophagus has a pH which is lower than that of the stomach, the processing of pH values may be used to accurately determine the position of the feeding portion of the tube structure.

Various modifications may be developed which are within the spirit and scope of the invention. These modifications may include, for example, using various types of electrodes and/or positioning a plurality of electrodes at preselectioned sites along the tube. Other modifications may also include attaching lights and/or alarms to the monitoring and/or position determining devices to alert personnel of a tube displacement.

I claim:

1. A system for introducing fluid material into a preselected area of the gastro-intestinal tract of a patient, and characterized by:
    an elongated flexible tube, said tube having a substantially axial lumen through which fluid can flow, a proximal end and a distal end, and having perforations therethrough along a preselected portion of the distal end of said tube, said perforations communicating from said lumen to the outside of said tube;
    means for introducing said fluid into said elongated flexible tube;
    pH measuring means positioned on said tube proximate to said distal end, for generating a signal representative of the pH of the body fluid adjacent to said distal end; and
    position means operatively connected to said pH measuring means for monitoring said adjacent pH signed and for determining the position of said distal end as a function of said monitored pH.

2. The system as described in claim 1 wherein said pH measuring means is positioned proximate to said perforations.

3. The system as described in claim 1 wherein said pH measuring means is positioned at a preselectd distance remote from said perforations.

4. The system described in claim 1, wherein said means for introducing fluid material into said tube is positioned at the proximal end thereof.

5. The system as described in claim 4, wherein said means for introducing comprises a controlled pump and control means for controlling the operation of said pump as a function of said position determination.

6. The system as described in claim 5, wherein said control means comprises means for turning off said pump upon a determination by said position means that said distal end is positioned outside of a predetermined position.

7. A system for introducing a fluid into the duodenum of a patient comprising:
    an elongated flexible tube having a proximal end and a distal end, said tube having a lumen therethrough for passing said fluid to about said distal end;
    port means at about the distal end of said tube for passing fluid through to the outside of said tube;
    pH measuring means integrally mounted at about the distal end of said tube for generating a pH signal representative of the pH of the body fluid in the area of said distal end;
    conductor means for providing electrical conduction between said pH measuring means and the proximal end of said tube;
    means connected to said conductor means at about the proximal end of said tube for receiving said pH signal and for providing therefrom an indication of the position of the distal end of said tube relative to the patient's duodenum; and
    means for introducing fluid into said tube at about the proximal end thereof.

8. A system for enteric feeding into the duodenum of a patient comprising:
    an elongated flexible tube having proximal and distal ends, said tube having a substantially axial lumen therethrough for passing fluid material, and perforations formed along the distal end of said tube for passing said fluid material through to the duodenum of a patient;
    an electrode integrally mounted to about the distal end of said tube and capable of measuring the pH of the body fluid adjacent to said electrode;
    conductor means for transmitting a signal from said electrode to an external pH monitoring device;
    a pH monitoring device connected to said conductor means at about the proximal end of said tube, and comprising a pH meter and means for comparing a value from said pH meter to a preselected limit to determine the position of the distal end as a function of pH;
    means for introducing fluid material into the proximal end of said tube;
    control means for generating a signal based upon the position determination; and
    means for terminating the introduction of fluid material into said proximal end of said tube upon the receipt of a signal from said control means, said signal indicating said tube is out of said duodenum.

9. The system of claim 8 in which said means for terminating the introduction of said fluid material is engaged upon receipt of two processed pH signals wherein the ratio of a first pH signal to a second pH signal is within a range of from about 2 to 12.

10. The system of claim 8 wherein said terminating means is a clamp.

11. A method for introducing a fluid into a patient's duodenum, said method utilizing an elongated flexible tube having means for communicating fluid from a proximal end to and out of a distal end thereof, having a sensor means for sensing pH in the area of said distal end, and providing a signal representative of sensed pH at about said proximal end, the method comprising:
    passing said tube through the gastrointestinal tract of said patient until said distal end is positioned in the patient's duodenum;
    sensing a pH signal with said sensor means in the area of said distal end;
    monitoring the pH in the area of the distal end of said tube by comparing said sensed pH signal with a reference value;
    determining when said distal end is and is not in said duodenum on the basis of said comparing; and
    introducing said fluid through said tube into said duodenum upon a determination that said distal end is in said duodenum.

12. The method of claim 11 comprising the steps of normally introducing fluid material through said tube for release into said duodenum, and inhibiting said fluid introduction upon a determination that said distal end is not in said duodenum.

13. The method of claim 12, wherein said inhibiting comprises automatically stopping introduction of said fluid material when said pH comparison indicates that said distal end is outside of said duodenum.

14. The method of claim 13, comprising the further steps of re-positioning said distal end within said duodenum upon said distal end becoming dislodged from said duodenum, and reintroducing said fluid material after said re-positioning.

15. A system for introducing a fluid into the duodenum of a patient comprising:

an elongated flexible tube having proximal and distal ends, said tube having a lumen therethrough for passing said fluid to about said distal end;

port means at about said distal end for passing fluid through to the outside of said tube;

pH measuring means integrally mounted on said tube proximal to said port means for generating a pH signal representative of the pH of the body fluid in the area of said port means;

conductor means for providing electrical conduction between said pH measuring means and the proximal end of said tube;

means connected to said conductor means at about the proximal end of said tube for receiving said pH signal and for providing therefrom an indication of the position of said pH measuring means; and means for introducing fluid into said tube at about the proximal end thereof.

* * * * *